United States Patent
Wang

(10) Patent No.: US 7,256,200 B2
(45) Date of Patent: Aug. 14, 2007

(54) METHOD AND COMPOSITION FOR POTENTIATING AN OPLATE ANALGESIC

(75) Inventor: Zaijie Wang, Oak Park, IL (US)

(73) Assignee: The Board of Trustees of the University of Illinois, a body corporate and politic of the State of Illinois, Urbana, IL (US)

( * ) Notice: Subject to any disclaimer, the term of this patent is extended or adjusted under 35 U.S.C. 154(b) by 268 days.

(21) Appl. No.: 10/769,536

(22) Filed: Jan. 30, 2004

(65) Prior Publication Data

US 2004/0220203 A1 Nov. 4, 2004

Related U.S. Application Data

(60) Provisional application No. 60/446,232, filed on Feb. 10, 2003.

(51) Int. Cl.
*A01N 43/42* (2006.01)
(52) U.S. Cl. ........................ 514/282; 514/117
(58) Field of Classification Search .................. None
See application file for complete search history.

(56) References Cited

U.S. PATENT DOCUMENTS

| | | | |
|---|---|---|---|
| 5,321,012 A | 6/1994 | Mayer et al. ............... 514/25 |
| 5,502,058 A | 3/1996 | Mayer et al. ............... 514/289 |
| 5,523,323 A * | 6/1996 | Maccecchini ............... 514/531 |
| 5,866,154 A | 2/1999 | Bahal et al. | |
| 6,043,224 A * | 3/2000 | Lee et al. ..................... 514/26 |
| 6,432,652 B1 | 8/2002 | Evans et al. | |
| 6,518,245 B1 * | 2/2003 | Anderson et al. ............. 514/14 |
| 6,869,440 B2 * | 3/2005 | Dobak, III ................. 607/105 |

FOREIGN PATENT DOCUMENTS

| | | |
|---|---|---|
| EP | 0 608 893 | 8/1994 |
| EP | 0 911 039 | 4/1999 |

OTHER PUBLICATIONS

FDA Approves Two Drugs to Treat Opiate Dependence, Forbes, Oct. 8, 2002, p. 1, http://www.webprowire.com/summaries/266443.html, printed Mar. 21, 2005.*
Vicodin Addiction, 2004, p. 1, http://www.vicodin-addiction.org/, printed Mar. 29, 2006.*
Fan G-H et al.: "Inhibition of Calcium/Calmodulin-Dependent Protein Kinase II in Rat Hippocampus Attenuates Morphine Tolerance and Dependence", 1999, Molecular Pharmacology, vol. 56. pp. 39-45.*
Gonzalez G. et al.: "Combating Opiate Dependence: A Comparison Among the Available Pharmacological Options", 2004, Expert Opin. Pharmacother. vol. 5. pp. 713-725.*
Wang et al. "Reversal of Morphine Antinociceptive Tolerance By Acute Spinal Inhibition of Ca/Calmodulin-Dependent Protein Kinase II", (Mar. 2003), European Journal of Pharmacology, vol. 465. pp. 199-200.*
A. Mestek et al., *The Journal of Neuroscience*, 15(3):2396-2406 (1995).
T. Koch et al., *Journal of Neurochemistry*, vol. 69, No. 4, 1767-1770 (1997).
L. Lou et al., *Molecular Pharmacology*, 55:557-563 (1999).
Z. Wang et al., *Life Sciences*, vol. 54, No. 20, pp. 339-350 (1994).
G-H. Fan et al., *Molecular Pharmacology*, 56:39-45 (1999).
P. Nitescu et al., *Eur. J. Pain*, 13, 3, 76-88 (1992).
Tan et al., "Trifluoperazine, an orally available clinically used drug, disrupts opioid antinoiceptive tolerance", Neuroscience Letters 2005 1-4.

* cited by examiner

*Primary Examiner*—Cecilia J. Tsang
*Assistant Examiner*—Hemant Khanna
(74) *Attorney, Agent, or Firm*—Licata & Tyrrell P.C.

(57) ABSTRACT

Composition and methods of treating pain and reducing, reversing, or preventing tolerance to opiate analgesics are disclosed. The composition and method utilize an opiate analgesic and a calcium calmodulin kinase (CaMKII) inhibitor as active agents to treat pain in mammals, including humans.

1 Claim, 4 Drawing Sheets

METHOD AND COMPOSITION FOR POTENTIATING AN OPIATE ANALGESIC

CROSS-REFERENCE TO RELATED APPLICATIONS

This application claims the benefit of U.S. provisional patent application Ser. No. 60/446,232, filed Feb. 10, 2003.

FIELD OF THE INVENTION

The present invention relates to the treatment of pain using an opiate analgesic and an inhibitor of calcium calmodulin dependent protein kinase (CaMKII). The composition and method permit prevention, reduction, or reversal of tolerance to an opiate analgesic in an individual undergoing opiate analgesic treatment by administering a therapeutically effective amount of an inhibitor of CaMKII. The present composition and methods also reduce the incidence of opiate analgesic addiction.

BACKGROUND OF THE INVENTION

One of the most significant health problems is an inadequate control of pain, especially chronic pain associated with diseases such as cancer, back pain, arthritis, and diabetic neuropathy. It is estimated that the annual cost for health care and lost productivity related to pain is over $100 billion in the U.S. One survey reported that nearly one-third of the U.S. population experiences chronic pain at some point in life. The impact of pain on society is measured not only in economic numbers, but, more importantly, by suffering. For example, more than 50 million Americans are partially or totally disabled by chronic pain, which accounts for about one-fourth of all workdays lost annually.

Analgesics are agents that relieve pain by acting centrally to elevate pain threshold, preferably without disturbing consciousness or altering other sensory functions. A mechanism by which analgesic drugs obtund pain (i.e., raise the pain threshold) has been formulated. Research in this area has resulted in the development of a number of opiate and opioid analgesics having diverse pharmacological actions. While opioid analgesics remain the mainstay for pain treatment, prolonged use of these drugs leads to tolerance that results in frequent dose escalation and increased side effects, such as altered cognitive state.

Opioid analgesics remain the preferred therapy for the treatment of moderate to severe pain, and of many painful chronic diseases. However, the chronic use of opioid drugs produces tolerance to these drugs. Whereas tolerance develops to essentially all opioid effects at varying rates, an attenuated analgesic effect is the most devastating clinic consequence because it leads to dose escalation and inadequate pain control, and possibly drug dependence.

Effective pain therapies directed to preventing opioid tolerance have long been sought. The success of developing such effective therapies requires a better understanding of the underlying tolerance mechanisms. Opioid receptor internalization, down-regulation, and uncoupling from G proteins (desensitization) all have been proposed as potential mechanisms. However, no consistent changes have been identified (Nestler, 1994; Nestler et al., 1997). A phenomena called "cAMP upregulation" has been proposed as a biochemical correlation for opioid tolerance (Sharma et al., 1975; Wang et al., 1994; Nestler, 1994). This theory was expanded when linked to the regulation of protein kinase A (PKA) and CREB activation in cellular model of opioid tolerance (Nestler, 1994; Nestler, 1997). However, studies with CREB mutant mice suggested that CREB may be a factor more important for opioid dependence (Maldonado et al., 1996; Blendy et al., 1998). Inhibition of PKA has produced an inconsistent effect on behavioral manifestations of opioid tolerance (e.g., Narita et al., 1995; Bilsky et al., 1996; Shen et al., 2000).

Other studies found that blocking NMDA receptor antagonists could prevent the development of, or disrupt established, opioid tolerance (Trujillo et al., 1991; Mao et al., 1995). Central to these findings is increased intracellular $Ca^{2+}$ levels resulting from NMDA receptor activation and other neuronal activation. Calcium ion ($Ca^{2+}$) is used as a second messenger in neurons, leading to the activation various protein kinases, among them, $Ca^{2+}$/phospholipids-dependent protein kinase (PKC) and $Ca^{2+}$/calmodulin-dependent protein kinase II (CaMKII). PKC has been implicated in opioid tolerance (Coderre et al., 1994; Mao et al., 1995; Granados-Soto et al., 2000; Narita et al., 2001). Mice lacking PKC exhibited significantly reduced opioid tolerance (Zeitz et al., 2001). NMDA receptors are known to interact with CaMKII by $Ca^{2+}$ influx and phosphorylation. It is unclear from these studies, however, whether CaMKII plays a role in the development and/or maintenance of opioid tolerance.

The available opiate and opioid analgesics are derivatives of five chemical groups (i.e., phenanthrenes, phenylheptylamines, phenylpiperidines, morphinans, and benzomorphans). Pharmacologically, these opiates and nonopiates differ significantly in activity. Some are strong agonists (morphine), while others are moderate-to-mild agonists (codeine). In contrast, some opiate derivatives exhibit mixed agonist-antagonist activity (nalbuphine), whereas others are opiate antagonists (naloxone). Morphine is the prototype of the opiate and opioid analgesics, all of which have similar actions on the central nervous system.

Morphine is an alkaloid chemically derived from opium papaver somniferum. Other drugs, such as heroin, are processed from morphine or codeine. Such opiates have been used both medically and nonmedically for centuries. By the early 19th century, morphine had been extracted in a pure form suitable for solution. With the introduction of the hypodermic needle, injection of a morphine solution became the common method of administration. Of the twenty alkaloids contained in opium, only codeine and morphine are still in widespread clinical use.

The opiates are among the most powerfully acting and clinically useful drugs producing depression of the central nervous system. Drugs of this group are used principally as analgesics, but possess numerous other useful properties. Morphine, for example, is used to relieve pain, induce sleep in the presence of pain, check diarrhea, suppress cough, ease dyspnea, and facilitate anesthesia.

However, morphine also depresses respiration; increases the activity and tone of the smooth muscles of the gastrointestinal, biliary, and urinary tracts causing constipation, gallbladder spasm, and urinary retention; causes nausea and vomiting in some individuals; and can induce cutaneous pruritus. In addition, morphine and related compounds have other properties that tend to limit their usefulness.

For example, when morphine and related compounds are administered over a long time period, tolerance to the analgesic effect develops, and the dose then must be increased periodically to obtain equivalent pain relief. Eventually, tolerance and physical dependence develop, which, combined with euphoria, result in excessive use and addiction of those patients having susceptible personalities. For these reasons, morphine and its derivatives must be used only as directed by a physician (i.e., not in greater dose, more often, or longer than prescribed), and should not be used to treat pain when a different analgesic will suffice.

Nevertheless, morphine remains the major drug for the treatment of moderate to severe pain (Foley, 1993). Opioids particularly are used to treat chronic painful conditions lacking a standard treatment, such as cancer pain, posttraumatic pain, postoperative pain, and neuropathic pain. However, opioid painkillers have significant adverse side effects like respiratory depression, nausea, vomiting, dizziness, sedation, mental clouding, constipation, urinary retention, and severe itching.

These adverse side effects limit the usefulness of opioids, like morphine, as painkillers. Therefore, several companies are developing a new generation of opioid painkillers, but advances in neuroscience have not progressed a sufficient extent to provide a significant breakthrough. Typically, companies are using proprietary technology to reformulate opioid drugs, such as morphine, into branded painkillers with improved clinical benefits. To date, innovations in the field of opioid painkillers have largely focused on increasing the convenience of opioid drugs. For example, important advances have been made in opioid delivery, such as sustained release formulations and transmucosal delivery.

CaMKII is a multifunctional calcium and calumodulin activated kinase, whose $\alpha$ and $\beta$ isoforms are abundant in the central nervous system. A vast amount of information is available for the interaction of CaMKII $\alpha$ isoform and NMDA receptor in longterm potentiation in hippocampal neurons, which is critical for learning and memory (e.g., Mayford et al., 1996). Glutamate can activate CaMKII through NMDA receptor and $Ca^{2+}$ influx in cultured rat hippocampal neurons (Fukunaga et al., 1992). Calcium influx via NMDA receptors results in activation and Thr286 autophosphorylation of CaMKII (Strack et al., 1998; Strack et al., 2000). On the other hand, CaMKII phosphorylates and activates the NMDA receptor, and enhances $Ca^{2+}$ influx through the channel (Kitamura et al., 1993).

No direct information exists for the role of CaMKII or NMDA/CaMKII interaction in opioid tolerance. Indirectly, chronic opioid administration increases both the level (Lou et al., 1999) and activity (Nehmad et al., 1982) of calmodulin, as well as calmodulin mRNA levels (Niu et al., 2000). Cytosolic free $Ca^{2+}$ also can be increased after treatment with opioids (Fields et al., 1997; Quillan et al., 2002). CaMKII also has been shown to phosphorylate and activate the cAMP response element binding protein (CREB) (Hokota et al., 2001). More direct evidence arose from the finding that CaMKII and $\mu$ opioid receptor ($\mu$OR) are colocalized in the superficial layers of the spinal cord dorsal horn, an area critical for pain transmission (Bruggemann et al., 2000). The cloned pOR contains several consensus sites for phosphorylation by CaMKII (Mestek et al., 1995). Desensitization of $\mu$OR was enhanced when CaMKII was overexpressed (Mestek et al., 1995; Koch et al., 1997). Recently, hippocampal, but not striatal, CaMKII was found to modulate opioid tolerance and dependence by affecting memory pathways (Fan et al., 1999; Lou et al., 1999). The role of spinal CaMKII in opioid tolerance is unknown.

The present invention is directed to the discovery that some pharmacological actions of morphine can be modified by coadministration of an inhibitor of CaMKII, hereafter termed a "CaMKII inhibitor."

SUMMARY OF THE INVENTION

Opioid analgesics are a mainstay in the field of pain treatment. However, the use of opioids to treat chronic pain leads to development of drug tolerance. A method and/or composition that prevents and/or reverses opioid tolerance would provide improved pain control in a large population of patients inadequately treated with opioid analgesics alone.

The present invention is directed to use of a CaMKII inhibitor in chronic pain therapy involving opiate analgesics, or administration of a CaMKII inhibitor to patients who develop a tolerance and/or addiction to opiate analgesics. Prevention or reversal of opiate tolerance by administration of a CaMKII inhibitor requires lower doses of opiate analgesics to treat pain, thus reducing the severity of various adverse side effects associated with high doses of opiate analgesics.

Accordingly, one aspect of the present invention is to provide a composition comprising a CaMKII inhibitor for use in treating pain in combination with an opiate analgesic, e.g., morphine.

The present invention also is directed to a method of reducing, reversing, or preventing tolerance to an opiate analgesic in an individual undergoing an opiate analgesic therapy by administering a CaMKII inhibitor to the individual. In the absence of an administered dose of a CaMKII inhibitor, the opiate analgesic dose would have to be increased over time to achieve the same pain-reducing effect. Administration of a CaMKII inhibitor allows the opiate analgesic to be administered at a constant, or reduced, dose to achieve a desired pain treatment. Administration of a CaMKII inhibitor to a patient who already developed tolerance to the opiate analgesic restores the effectiveness of a low dose of opiate analgesics. The constant or reduced amount of opiate analgesic required to provide a desired pain-reducing effect thus reduces the severity of various adverse side effects associated with opiate analgesic treatment, and reduces the possibility of opiate analgesic dependence.

The present invention also provides a method for improved pain treatment. In particular, the present invention is directed to methods of administering an opiate analgesic and a CaMKII inhibitor to prevent and/or treat chronic pain. More particularly, the present invention is directed to compositions containing an opiate analgesic, like morphine, and a CaMKII inhibitor, and to use of an opiate analgesic and a CaMKII inhibitor, administered simultaneously or sequentially, in methods of treating pain, and reducing, reversing, and preventing opiate analgesic tolerance and dependence.

An important aspect of the present invention, therefore, is to provide a method and composition for preventing or treating pain, while reducing the occurrence or severity of adverse side effects associated with opiate analgesic treatment.

Another aspect of the present invention is to reduce the problem of dependence and addiction associated with present opiate analgesics used to treat pain by administration of a therapeutically effective amount of a CaMKII inhibitor to an individual undergoing opiate analgesic treatment.

Still another aspect of the present invention is to provide a method of reducing or reversing opiate analgesic tolerance in an individual undergoing an opiate analgesic therapy by administering a therapeutically effective amount of a CaMKII inhibitor to the individual.

Yet another aspect of the present invention is to provide an article of manufacture for human pharmaceutical use, comprising (a) a package insert, (b) a container, and either (c1) a packaged composition comprising an opiate analgesic and a CaMKII inhibitor or (c2) a packaged composition comprising an opiate analgesic and a packaged composition comprising a CaMKII inhibitor.

Another aspect of the present invention is to provide a method of screening candidate compounds for a CaMKII inhibitor by monitoring CaMKII activity and expression in morphine-tolerant rats and cell models.

These and other aspects of the present invention will become apparent from the following detailed description of the preferred embodiments of the invention.

DETAILED DESCRIPTION OF THE PREFERRED EMBODIMENTS

Figure 1:
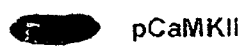
FIG. 1 shows the detection of active CaMKII in SH-SY5Y human neuroblastoma cells by a Western blotting method.

Currently no therapy or adjuvant therapy exists for the prevention or reversal of opioid tolerance. When tolerance occurs, which is inevitable in all prolonged users of an opiate analgesic, the treatment choice is dose-escalation, which leads to increased adverse side effects, including a higher probability of drug dependence. In some cases, tolerance occurs so dramatically and quickly that even a large dose increase may not control pain.

The present invention is directed to the simultaneous or sequential administration of an opiate analgesic and a CaMKII inhibitor to prevent and/or treat pain. In particular, administration of morphine and a CaMKII inhibitor to rats shows that a CaMKII inhibitor restores the effectiveness of morphine in animals that are tolerant to even very large doses of morphine. Accordingly, the dose of morphine can be reduced, while providing an analgesic effect equivalent to administering a higher dose of morphine alone. The reduced dose of morphine also reduces adverse side effects associated with morphine administration, and can significantly reduce the addiction potential of morphine in susceptible individuals.

The present invention also is directed to the administration of a CaMKII inhibitor to an individual undergoing an opiate analgesic therapy to reduce or reverse opiate analgesic tolerance in the individual. The administration of a CaMKII inhibitor allows the dose of an opiate analgesic to remain constant, or to be reduced, while maintaining the desired pain-reducing effect. By reducing or reversing tolerance to an opiate analgesic, the occurrence of adverse side effects can be reduced, and the possibility of opiate analgesic dependence is reduced.

The present invention, therefore, provides compositions and methods of reducing or reversing tolerance to opiate analgesics, thus potentiating the analgesic properties of an opiate analgesic. The present invention also provides pharmaceutical compositions comprising an opiate analgesic and a CaMKII inhibitor. Further provided are articles of manufacture comprising an opiate analgesic and a CaMKII inhibitor, packaged separately or together, and an insert having instructions for using the active agents.

The methods described herein benefit from the use of an opiate analgesic and a CaMKII inhibitor in the treatment and management of pain. The analgesic and CaMKII inhibitor can be administered simultaneously or sequentially to achieve the desired effect of pain treatment or reduction or reversal of opiate analgesic tolerance.

For the purposes of the invention disclosed herein, the term "treatment" includes preventing, lowering, or eliminating pain. As such, the term "treatment" includes both medical therapeutic and/or prophylactic administration, as appropriate.

The term "container" means any receptacle and closure therefore suitable for storing, shipping, dispensing, and/or handling a pharmaceutical product.

The term "insert" means information accompanying a product that provides a description of how to administer the product, along with the safety and efficacy data required to allow the physician, pharmacist, and patient to make an informed decision regarding use of the product. The package insert generally is regarded as the "label" for a pharmaceutical product.

The phrase "reducing or reversing opiate analgesic tolerance" is defined as the ability of a compound to reduce the dosage of an opiate analgesic administered to an individual to maintain a level of pain control previously achieved using a greater dosage of opiate analgesic.

Several mechanisms have been proposed as playing a role in the action of morphine and morphine tolerance and dependence. However, the mechanisms underlying opioid tolerance is not entirely understood. A number of studies have been initiated to address signal transduction pathways that contribute to the behavioral manifestation of tolerance. Those studies have greatly advanced understanding of the mechanism of opioid tolerance, and potentially can lead to improved pain therapies.

It now has been shown that calcium calmodulin dependent protein kinase (CaMKII) is important in promoting and maintaining opioid tolerance. This finding is the result of tests using a rodent model for opioid tolerance based on a commercially available CaMKII inhibitor, i.e., KN93 (2-[N-(2-hydroxyethyl)]-N-(4-methoxybenzenesulfonyl)]amino-N-(4-chlorocinnamyl)-N-methylbenzylamine). Further support for this finding is the upregulation of CaMKII expression in rats that are tolerant to morphine. Thus, modulation of CaMKII signaling pathways can be used to prevent and reverse opioid tolerance. The present invention, therefore, provides a novel method of managing pain, reducing dependence on opioids, and reducing tolerance to opioids.

Morphine is a major drug for the treatment of moderate to severe pain (Foley, 1993). Morphine primarily is used to treat severe pain associated with trauma, myocardial infarction, and cancer. Although, morphine is one of the most effective painkillers, effective pain management requires that adequate analgesia be achieved without excessive adverse side effects. Many patients treated with morphine are not successfully treated because of excessive adverse side effects and/or inadequate analgesia. For example, the use of morphine in the treatment of chronic pain is limited because of inadequate analgesia.

Management of excessive adverse side effects associated with morphine administration remains a major clinical challenge. Numerous strategies have been advanced to address this problem, such as (i) switching opioids, (ii) changing routes of opioid administration, (iii) improved opioid formulations, (iv) clonidine treatment, and (v) coadministrating opioids that act on different receptors.

A substantial research effort directed to the development of opioid analgesics resulted in the discovery of numerous compounds having a varying affinity and efficacy at all the known opioid receptor subtypes. Although compounds of extremely high potency have been produced, the problem of tolerance to, and dependence on, these agonists persists (Williams et al., 2001).

For example, the chronic administration of morphine results in the development of physical dependence, as evidenced by the appearance of distressing physical symptoms induced by abrupt termination of morphine treatment. The signs and symptoms simulate a severe cold, and usually include nasal discharge, lacrimation, chills, goose pimples, muscular aches, enhanced motor reflexes, profound body water loss attributed to hyperthermia, hyperventilation, emesis, and diarrhea (Himmelsbach, 1943; Katz et al., 1986; Maldonado et al., 1996; Quock et al., 1968). It is well known that various types of opioid receptors are involved in the development of the psychological and physical dependence on opioids.

The opioid receptors have been classified as μ, δ, and κ receptors, based on the relative affinity shown for experimental opioid receptor ligands. μ-Opioid receptors have been reported to play a dominant role in several pharmacological effects of morphine.

Role of μ-opioid Receptors

An intracerebroventricular (i.c.v) injection of a selective and irreversible μ-opioid receptor antagonist, i.e., β-funaltrexamine (β-FNA), drastically antagonizes morphine induced antinociception (Portoghese et al., 1980; Takemori et al., 1981; Ward et al., 1982). β-FNA also inhibits the development of physical dependence on morphine in rats (Aceto et al., 1986; DeLander et al., 1984). Administration of a selective μ-opioid receptor antagonist, i.e., D-Phe-Cys-Tyr-D-Trp-Arg-The-Pen-Thr-NH$_2$, into the lateral cerebral ventricle 72 hours after subcutaneous implantation of two 75 mg pellets of morphine in rats induces a severe withdrawal syndrome (Maldonado et al., 1992). The knockout mice with deleted μ-opioid receptors display neither analgesia from morphine or other clinically used opiates, nor expression of naloxone-precipitated withdrawal symptoms including jumping and body weight loss (Matthes et al., 1996). This data and other pharmacological studies indicate that the μ-opioid receptors predominantly mediate the analgesic and rewarding effect of opioids.

Role of δ-opioid Receptors

Studies suggest that an interaction exists between μ- and δ-opioids. It has been found that at subantinociceptive doses, δ-opioid receptor agonists modulate antinociceptive responses to μ-opioid receptor agonists in mice (Jiang et al., 1990). Morphine acts mainly at the μ-receptor sites, but also can interact with δ-opioid receptors in vivo and in vitro (Narita et al., 1993). δ-Opioid receptor antagonists do not effect morphine antinociceptive action. However, the selective blockade of δ-opioid receptors by naltrindole (NTI) inhibits the development of physical dependence on morphine (Suzuki et al., 1997).

Role of κ-opioid Receptors

Increasing evidence indicates that activation of κ-opioid receptors opposes a variety of μ-opioid receptor mediated actions throughout the brain and spinal cord (Pan, 1998). Treatment with nor-binaltorphimine (nor-BNI), a selective κ-opioid receptor antagonist, when compared to naloxone, did not precipitate weight loss or other withdrawal signs in morphine-dependent mice (Cowan et al., 1988). Pretreatment with nor-BNI during chronic morphine treatment displays aggravation of weight loss precipitated by naloxone in morphine-dependent mice and rats (Suzuki et al., 1992). These studies indicate that antagonism of endogenous κ-opioidergic system apparently elicits a potentiating effect on some morphine-withdrawal signs, including weight loss. Stimulation of endogenous κ-opioidergic system therefore should attenuate morphine withdrawal symptoms. Dynorphin A has been reported to inhibit morphine withdrawal symptoms induced by naloxone precipitation or morphine discontinuation in morphine dependent animals (Suzuki et al., 1992). However, 3,4-dichloro-N-methyl-N-[2-(1-pyrrolidinyl)cyclohexyl]benzeneacetamide (i.e., U-50,488H), a selective κ-opioid receptor agonist, did not suppress the development of physical dependence on morphine in rats (Fukagawa et al., 1989). This difference has been attributed to the action of dynorphin A on all three subtypes of κ-opioid receptors, while U-50,488H acts mainly on $κ_1$-opioid receptor subtype (Narita et al., 2001).

In summary, μ- and δ-opioid receptors show morphine-like withdrawal symptoms, while κ-opioid agonists do not. An opposing interaction occurs between μ/δ-opioid agonists and κ-opioid agonists.

Role of Nonopioid Receptors in Morphine Actions

Numerous studies, including molecular and genetic approaches, suggest a substantial role of μ-opioid receptors in the development of morphine dependence and in numerous other actions of morphine. However, other systems also are involved. A role for 5-HT and cholecystokinin systems, as well as N-methyl-D-aspartate (NMDA) receptors, in opioid place conditioning has been proposed (Van Ree et al., 1999).

In particular, a number of studies have implicated important roles of NMDA receptor and protein kinase C mediated phosphorylation in opioid tolerance. NMDA receptors also can be regulated upon phosphorylation by calcium calmodulin kinase II (CaMKII). However, no direct evidence links the latter with opioid tolerance.

It has been widely reported that prototypical NMDA receptor antagonists dizocilpine and ketamine, which have similar affinity for NR1/NR2A and NR1/NR2B receptors (Varney et al., 1996), suppress morphine-induced place preference (Avenet et. al., 1997; Tzschentke et al., 1995). Evidence is accumulating that the NR2B subunit of NMDA receptors in the nucleus accumbens may be involved in the rewarding effect of morphine (Standaert et al., 1994; Watanabe et al., 1993). Neuroadaptive changes in specific brain regions that generate opioid dependence have been identified as noradrenergic transmission originating in the locus ceruleus, and most likely play the primary causal role in the expression of physical dependence on opioids. In contrast, a combination of behavioral and neurobiological studies point to the mesolimbic dopaminergic pathway projecting from the ventral tegmental area to the nucleus accumbens as a critical site for the initiation of psychological dependence on opioids.

In accordance with an important feature of the present invention, it has been discovered that chronic actions of morphine and related opioids (e.g., tolerance and dependence), but not the acute action of morphine and related opioids (e.g., analgesia), can be modulated by CaMKII inhibitors. This approach is particularly useful for the management of symptoms of morphine withdrawal.

In accordance with another important feature of the present invention, an opiate analgesic is present in a composition, or is administered, with a CaMKII inhibitor in a weight ratio of analgesic-to-inhibitor of about 0.01:1 to about 100:1, preferably about 0.02:1 to about 50:1, and most preferably about 0.1:1 to about 10:1. This ratio depends upon the type and identity of opioid analgesic and CaMKII inhibitor being used. The ratio of analgesic-to-inhibitor that is administered is dependent upon the particular analgesic and inhibitor used, and the origin and severity of the pain being treated. This ratio can be readily determined by a person skilled in the art to achieve the desired reduction in pain.

An opiate analgesic utilized in the present invention can be one or more opium alkaloid or semisynthetic opiate analgesic. Specific opiate analgesics include, but are not limited to, (a) opium; (b) opium alkaloids, such as morphine, morphine sulfate, codeine, codeine phosphate, codeine sulfate, diacetylmorphine, morphine hydrochloride, morphine tartrate, and diacetylmorphine hydrochloride; and (c) semisynthetic opiate analgesics, such as dextromethorphan hydrobromide, hydrocodone bitartrate, hydromorphone, hydromorphone hydrochloride, levorphanol tartrate, oxymorphone hydrochloride, and oxycodone hydrochloride. Other opioids include, but are not limited to, fentanyl, meperidine, methodone, and propoxyphene.

A CaMKII inhibitor utilized in the present invention can be any of the CaMKII inhibitors known in the art. The CaMKII inhibitors include, but are not limited to, chemical inhibitors that operate on the catalytic and regulatory, linker, association, and other domains of CaMKII; small peptides based on the CaMKII protein sequence capable of specifically inhibiting CaMKII; antisense oligonucleotide inhibitors; and short interfering RNA duplexes (siRNA).

Specific CaMKII inhibitors include, but are not limited to:

1. Chemical Inhibitors

A. Inhibitors that Operate on the Catalytic and Regulatory, Linker, and Association Domains of CaMKII
KN62 (Kamiya Biomedical, Thousand Oaks, Calif.)
KN93
H89
HA1004
HA1077
Autocamtide-2 related inhibitory peptide (AIP), and the myristoylated form thereof
K-252a
Staurosporine
Lavendustin C B. Calcium Chelators
BAPTA, tetrasodium salt
5,5'-Dibromo-BAPTA, tetrasodium salt
BAPTA/AM
5,5'-Difluoro-BAPTA/AM,
EDTA, tetrasodium salt (Ethylenediamine tetraacetic acid)
EGTA (Ethylenebis(oxyethylenenitrilo)tetraacetic acid)
EGTA/AM
MAPTAM
TPEN C. Calmodulin Antagonists
Calmidazolium chloride
Calmodulin binding domain
Chlorpromazine
Compound 48/80

Fluphenazine-N-2-chloroethane dihydrochloride
Melittin
Ophiobolin A
Pentamidine isethionate
Phenoxybenzamine
Trifluoperazine
W-5
W-7
W-12
W-13

2. Small Peptides Based on the CaMKII Protein Sequence
CaMKII 290-309, (i.e., H-Leu-Lys-Lys-Phe-Asn-Ala-Arg-Arg-Lys-Leu-Lys-Gly-Ala-Ile-Leu-Thr-Thr-Met-Leu-Ala-OH)

[Ala286]CaMKII Inhibitor 281-301 (i.e., MHRQEAVD-CLKKFNARRKLKG)

CaMKII Inhibitor 281-309 (i.e., MHRQETVD-CLKKFNARRKLKGAILTTMLA)

Similar longer, shorter, and neighboring protein sequences

3. Nucleic Acid-based Inhibitors

The CaMKII inhibitors can be based on the use of nucleic acid-based techniques to block the expression of CaMKII, and, therefore, to perturb the activity of CaMKII. Polynucleotide gene products are useful in this endeavor include antisense polynucleotides, ribozymes, RNAi, and triple helix polynucleotides that modulate the expression of CaMKII. Antisense polynucleotides and ribozymes are well known to those of skill in the art. Crooke and B. Lebleu, eds., "Antisense Research and Applications" (1993) CRC Press; and "Antisense RNA and DNA" (1988) D. A. Melton, Ed., Cold Spring Harbor Laboratory Cold Spring Harbor, N.Y. Antisense RNA and DNA molecules act to directly block the translation of mRNA by binding to targeted mRNA and preventing protein translation. An example of an antisense polynucleotide is an oligodeoxyribonucleotide derived from the translation initiation site, e.g., between −10 and +10 regions of the relevant nucleotide sequence.

Although antisense sequences may be directed against the full length genomic or cDNA of CaMKII, they also can be shorter fragments or oligonucleotides, e.g., polynucleotides of 100 or less bases. Although shorter oligomers (8-20) are easier to prepare and are more permeable in vivo, other factors also are involved in determining the specificity of base pairing. For example, the binding affinity and sequence specificity of an oligonucleotide to its complementary target increases with increasing length. It is contemplated that oligonucleotides of 8, 9, 10, 11, 12, 13, 14, 15, 16, 17, 18, 19, 20, 25, 30, 35, 40, 45, 50, or more base pairs will be used.

Ribozymes are enzymatic RNA molecules capable of catalyzing the specific cleavage of RNA. The mechanism of ribozyme action involves sequence specific interaction of the ribozyme molecule to complementary target RNA, followed by an endonucleolytic cleavage. Within the scope of the invention are engineered hammerhead or other motif rlbozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU, and GUC. Once identified, short RNA sequences of between 15 and 20 ribonucleotides corresponding to the region of the target gene containing the cleavage site can be evaluated for predicted structural features, such as secondary structure, that may render the oligonucleotide sequence unsuitable. The suitability of candidate targets also can be evaluated by testing their accessibility to hybridization with complementary oligonucleotides, using ribonuclease protection assays. See, PCT WO 93/2356; and U.S. Pat. No. 5,093,246.

Nucleic acid molecules used in triple helix formation for the inhibition of transcription generally are single stranded and composed of deoxyribonucleotides. The base composition is designed to promote triple helix formation via Hoogsteen base pairing rules, which generally require sizeable stretches of either purines or pyrimidines to be present on one strand of a duplex. Nucleotide sequences can be pyrimidine-based, which results in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules can be selected that are purine-rich, for example, containing a stretch of G residues. These molecules form a triple helix with a DNA duplex that is rich in GC pairs, wherein the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Another technique that is of note for reducing the or disruption the expression of a gene is RNA interference (RNAi). The term "RNA interference" was first used by researchers studying *C. elegans* and describes a technique by which post-transcriptional gene silencing (PTGS) is induced by the direct introduction of double stranded RNA (dsRNA: a mixture of both sense and antisense strands). Injection of dsRNA into *C. elegans* resulted in much more efficient silencing than injection of either the sense or the antisense strands alone (Fire et al., Nature, 391:806-811, 1998). Just a few molecules of dsRNA per cell is sufficient to completely silence the expression of the homologous gene. Furthermore, injection of dsRNA caused gene silencing in the first generation offspring of the *C. elegans* indicating that the gene silencing is inheritable (Fire et al., Nature, 391:806-811, 1998). Current models of PTGS indicate that short stretches of interfering dsRNAs (21-23 nucleotides; siRNA also known as "guide RNAs") mediate PTGS. siRNAs are apparently produced by cleavage of dsRNA introduced directly or via a transgene or virus. These siRNAs may be amplified by an RNA-dependent RNA polymerase (RdRP) and are incorporated into the RNA-induced silencing complex (RISC), guiding the complex to the homologous endogenous mRNA, where the complex cleaves the transcript.

While most of the initial studies were performed in *C. elegans*, RNAI is gaining increasing recognition as a technique that may be used in mammalian cell. It is contemplated that RNAi may be used to disrupt the expression of a gene in a tissue-specific manner. By placing a gene fragment encoding the desired dsRNA behind an inducible or tissue-specific promoter, it should be possible to inactivate genes at a particular location within an organism or during a particular stage of development. Recently, RNAi has been used to elicit gene-specific silencing in cultured mammalian cells using 21-nucleotide siRNA duplexes (Elbashir et al., Nature, 411:494-498, 2001). In the same cultured cell systems, transfection of longer stretches of dsRNA yielded considerable nonspecific silencing. Thus, RNAi has been demonstrated to be a feasible technique for use in mammalian cells and could be used for assessing gene function in cultured cells and mammalian systems, as well as for development of gene-specific therapeutics.

Antisense RNA and DNA molecules, ribozymes, RNAi and triple helix molecules can be prepared by any method known in the art for the synthesis of DNA and RNA molecules. These include techniques for chemically synthesizing-oligodeoxy-ribonucleotides well known in the art including, but not limited to, solid phase phosphoramidite chemical synthesis. Alternatively, RNA molecules can be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably or transiently into cells.

Preferred CaMKII inhibitors include KN93, 10.KN62, CaMKII Inhibitor 281-309, and mixtures thereof.

The following is a description of tests conducted to illustrate the potentiating effects of a CaMKII inhibitor on an opiate analgesic administered to a mammal, including humans.

Overall, the test results demonstrate that a CaMKII inhibitor prevents the development of tolerance to analgesic actions of opiate analgesics, like morphine. A CaMKII inhibitor also has been found to prevent or reverse both the development of tolerance to analgesic opiates and physical dependence.

The present studies provide information that CaMKII promotes and/or maintains opioid tolerance. Although some evidence exists that intracellular calcium and calmodulin can be increased after opioid treatment, it is not known if CaMKII can directly modulate opioid tolerance. The finding that spinal CaMKII is an essential mediator of opioid tolerance is determined by the following experiments. In addition, the studies correlate the inhibition of CaMKII with opioid tolerance. The results of the present studies illustrate the role of spinal CaMKII in opioid tolerance, which led to the present novel pain therapy.

Preliminary tests have shown that CaMKII is an important element in promoting and maintaining opioid tolerance. For example, it now has been shown that spinal calcium calmodulin kinase II (CaMKII) activity is increased in rats rendered tolerant to morphine. In addition, spinal administration of a CaMKII inhibitor can reverse morphine antinociceptive tolerance.

The following tests were performed to show that CaMKII is a key factor in promoting opioid tolerance: 1) investigation of the activation of CaMKII by acute treatment with morphine in SH-SY5Y cells, and the dose-response and time-course of this effect; and 2) correlation of the activation of CaMKII and morphine antinociceptive tolerance in vivo. A CaMKII inhibitor is applied over a full dose range in a rat model of opioid tolerance to illustrate that inhibition of CaMKII reverses morphine antinociceptive tolerance.

A1. Acute Treatment with an Opioid Receptor Agonist (Morphine) Activates CaMKII, which is Reversed by an Opioid Receptor Antagonist (Naloxone)

A test was performed to determine whether morphine activates CaMKII in human neuroblastoma SH-SY5Y cells. The test can be performed directly in animals, however, the experiments are performed more quickly in a large scale, both for dose response and time course, in a cell line that endogenously expresses both opioid receptors and CaMKII. In addition, establishment of such an effect in a cell line provides an in vitro model for additional studies directed to the mechanism of CaMKII activation by opioids. The results of this test were compared and correlated to test results from in vivo studies discussed below.

A. Determination of the Time Course of CaMKII Activation by Morphine, and its Reversal by Naloxone SH-SY5Y cells were treated with a high concentration of morphine for various lengths of time to determine whether CaMKII is activated by morphine, as determined by Western blotting using a specific antibody recognizing activated CaMKII, and the time course thereof. Another test determined whether activation of CaMKII by morphine is blocked by the opioid receptor antagonist naloxone.

B. Construction of the Dose Response-curve of Morphine in Activating CaMKII

SH-SY5Y cells were treated with increasing concentrations of morphine (0.1 nM to 100 μM) to determine the dose-dependent activation of CaMKII. The cells were treated with morphine for a sufficient duration to observe the peak activation effect, as determined in paragraph A above. The effect of morphine on CaMKII was compared to its inhibition of cAMP accumulation in SH-SY5Y cells (see following paragraph C).

C. Testing the Dose-response of Morphine on Inhibition of cAMP Accumulation

Activation of opioid receptors leads to the inhibition of cAMP production via G protein (Gi), which is used to determine the activation of opioid receptors by morphine. SH-SY5Y cells were challenged with increasing concentrations of morphine to construct a dose-response curve for inhibition of cAMP accumulation.

A2. CaMKII Expression and Activity are Regulated by Opioid Tolerance

Experiments designed to directly test whether CaMKII is important in driving and/or maintaining opioid antinociceptive tolerance were performed. Changes in CaMKII expression and/or activity were linked to the development of morphine antinociceptive tolerance, and compared to activation of CaMKII in cells from A1. above.

A. Determination of Whether Morphine Increases CaMKII Expression and Activity, and Whether the Changes Exhibit a Temporal Correlation with the Development of Morphine Tolerance Rats first were made tolerant by subcutaneous implantation of morphine pellets. Changes in spinal CaMKII expression and activity in the tolerant rats, compared to changes in placebo pelleted rats, were analyzed over time.

B. Determination of Antinociceptive Tolerance to Morphine

Antinociceptive tolerance to morphine was studied in rats receiving morphine pellets by constructing dose-response curves for subsequent morphine administration, and by following the decreasing morphine antinociception over time. The onset of antinociceptive tolerance was correlated to the changes in spinal CaMKII expression and activity.

A3. A CaMKII Inhibitor Reverses Opioid Tolerance

Tests were performed to further demonstrate the positive effects of a CaMKII inhibitor by correlating inhibition of CaMKII activity with the development of morphine antinociceptive tolerance. A selective CaMKII inhibitor, i.e., KN93, was used to inhibit CaMKII and reverse morphine tolerance. As a control, KN92 also was used. KN92 is a structural analog of KN93, but does not inhibit CaMKII.

A. Inhibition of CaMKII by KN93

KN93 was administered intrathecally (i.th.), and the time- and dose-dependent inhibition of CaMKII in the lumbar spinal cord was determined. Doses of KN93 that produced significant inhibition of CaMKII activity were used for the studies discussed below.

B. Determination of Whether KN93 Reverses an Established Morphine Antinociceptive Tolerance in Rats, and Whether the Reversal Correlates with the Inhibition of CaMKII Activity Rats first were made morphine tolerant. At peak tolerance, KN93 was injected intrathecally to the morphine-tolerant rats, before analgesic testing, to determine whether KN93 acutely reverses morphine tolerance. The KN93 dose response effect on reversing morphine tolerance was compared to its effect in inhibiting CaMKII activity.

B. Tests and Data

B1. Expression of CaMKII in SH-SY5Y Cells

These tests investigated the expression of CaMKII in human neuroblastoma SH-SY5Y cells. SH-SY5Y cells were grown in Dulbecco's modified eagle medium (DMEM) supplemented with 10% fetal calf serum, 100 μg/ml streptomycin, and 100 units/ml penicillin (Wang et al., 2000). To detect the expression of CaMKII/cells were harvested, homogenized, and solubilized in RIPA buffer in the presence of protease inhibitors (see Section C10). After a 45-minute centrifugation at 48,000×g, aliquots of the supernatant sample (30 μg total protein) were used to detect the activated CaMKII (pCaMKII) by Western blotting (Section C10) using a polyclonal antibody recognizing CaMKII. FIG. 1 illustrates detection of active CaMKII (pCaMKII) in SH-SY5Y human neuroblastoma cells by Western blotting method. A specific band at about 50 kd, corresponding to the pCaMKII α isoform, was detected in SH-SY5Y cells (FIG. 1). Whether CaMKII activity is regulated by morphine treatment also was examined.

B2. Inhibition of Intracellular cAMP Accumulation by Morphine

Figure 2:
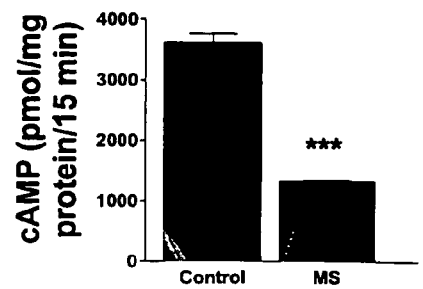
FIG. 2 contains bar graphs for cAMP (pmol/mg protein/15 min) for morphine inhibited cAMP accumulation in SH-SY5Y cell in the presence (MS) and absence (control) of morphine.

Inhibition of cAMP accumulation was used to measure the activation of opioid receptors by morphine. SH-SY5Y cells were plated in 24 well dishes one week before the assay. For the cAMP assay, cells were incubated with 10 μM forskolin and 250 μM 3-isobutyl-1-methylxanthine in the presence or absence of morphine (10 μM) at 37° C. for 15 minutes. Intracellular cAMP content was analyzed by a radioimmunoassay. FIG. 2 shows that morphine inhibited cAMP accumulation in SH-Sy5Y cells. Cells were incubated with 10 μM forskolin and 250 μM 3-isobutyl-1-methylxanthine in the presence ("MS") or absence ("Control") of 10 μM morphine. Morphine significantly reduced cAMP accumulation (***$p<0.001$). In particular, morphine (10 μM) inhibited cAMP accumulation by 63% ($p<0.001$), indicative of opioid receptor activation (FIG. 2). A dose-response curve for morphine was compared with its action on CaMKII.

B3. KN93 Reverses an Established Morphine Antinociceptive Tolerance

Figure 3:
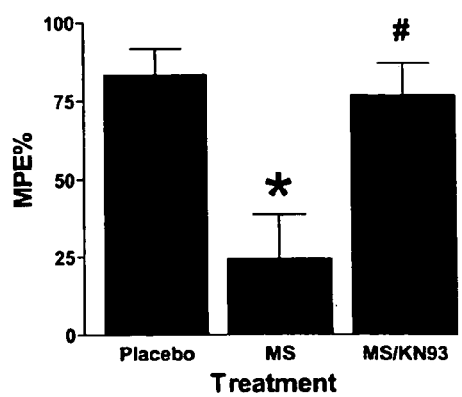
FIG. 3 contains bar graphs for MPE % for a placebo, morphine treated, and morphine/KN93 treated groups.

Tests were performed to determine whether spinally applied KN93, a CaMKII inhibitor, disrupts morphine antinociceptive tolerance in rats. Individual groups of eight rats were implanted with i.th. catheters and allowed to recover for 5 to 7 days. Then, the rats were implanted subcutaneously (s.c.) with either morphine (two 75 mg pellets/rat, NIDA) or placebo pellets. Baseline nociception and morphine antinociceptive effects were tested prior to pelleting. Five days after pelleting, the rats were tested for latencies in tail-flick test using 52° C. warm water before and 30 minutes after i.th. acute injection of morphine (10 µg in 5 µl saline). FIG. 3 shows that chronic morphine treatment produced antinociceptive tolerance to i.th. morphine (p<0.05). The reduced morphine antinociceptive. effect in morphine-pelleted rats ("MS") was reversed by i.th. administration of KN93 (15 nmol/5pl saline) 15 minutes before the i.th. morphine (i.e., 45 minutes before tail-flick testing) ("MS/KN93") (*p<0.05 compared to "Placebo" group; #p<0.05 compared to "MS" group). Morphine had a significantly reduced antinociceptive effect in morphine-pelleted animals compared to the effect of morphine in rats received placebo pellets (FIG. 3), or prepelleting baseline (data not shown).

These results indicate that the rats are morphine tolerant. Morphine antinociceptive tolerance was blocked by administration of KN93 (15 nmol in 5:1 saline, i.th. injection) 15 minutes before acute challenge of morphine (FIG. 3). KN93 alone did not alter basal nociception, nor did KN93 affect morphine-antinociception in naïve rats (data not shown). In other experiments, the dose-response effect of KN93 in reversing or preventing morphine tolerance (by constructing and comparing dose-response curves of i.th. morphine), and the dose dependent inhibition of CaMKII activity, were investigated.

B4. Spinal CaMKII Activity is Enhanced in Morphine Tolerance

Figure 4:
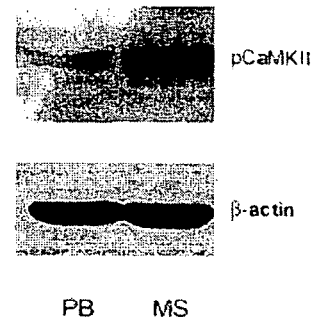
FIG. 4 contains plots showing that morphine treatment increased CaMKII activity.

Tests were performed to determine the correlation between CaMKII activity and morphine tolerance. FIG. 4 shows that morphine treatment increased CaMKII activity. Lumbar spinal cord segments were taken from placebo ("PB") or morphine ("MS") pelleted rats for the analysis of active CaMKII (pCaMKII). β-Actin was used as the internal control for quantitative comparision between samples. The average increase of CaMKII activity from two pairs of animals was 250%. Spinal CaMKII activity, as measured by the active CaMKII (pCaMKII) content, was increased (FIG. 4) in rats made tolerant to morphine as described in paragraphs C8 and B3. Test results demonstrated the important role of CaMKII in opioid tolerance. The temporal correlation between morphine tolerance and changes in CaMKII activity and/or expression also were investigated.

C. Research Design, Methods, and Rationale

C4 through C12 disclose the methodology applied to test the ability of a CaMKII inhibitor to reduce tolerance to morphine and other opiate analgesics.

C1.

Tests were performed to determine whether a clinically used opioid receptor agonist, i.e., morphine, activates CaMKII in the human neuroblastoma SH-SY5Y cells. It was found that intracellular free calcium and calmodulin both increased after treatment with morphine in cultured cells. Based on these findings, it was theorized that morphine activates CaMKII. Accordingly, tests were performed to establish that CaMKII, in particular CaMKIIα, is activated by morphine. As described above, this test can be performed directly in animals. However, the experiments can be performed more rapidly in cell culture. The results of this test were compared to test results from in vivo studies.

C1A. Experimental Design to Demonstrate the Time Course of CaMKII Activation by Morphine, and its Reversal by Naloxone Separate dishes of triplicate SH-SY5Y cells were treated with a high concentration of morphine (10 µM) for various lengths of time (0, 0.5, 1, 5, 10, 30, 60, 120, 240, 360 minutes) to determine whether CaMKII is activated. At the end of the treatment, cells were harvested for analyses of CaMKII activity by Western blotting using an antibody specifically recognizing activated CaMKII (pCaMKII). Samples also were analyzed using antibodies specific for total CaMKII and β-actin, which were used for quantitative comparison between control and treated groups. In a separate experiment, when a maximum effect was observed, cells were incubated with morphine in the presence of the opioid receptor antagonist naloxone (10 µM) to verify that the effect of morphine is mediated by the opioid receptors. All experiments were repeated at least three times for statistical comparisons.

C1B. The Dose Response-curve of Morphine in Activating CaMKII

In these experiments, separate dishes of SH-SY5Y cells were treated with increasing concentrations of morphine (0.1 nM to 100 µM) to determine the dose-dependent activation of CaMKII. The treatment time is the maximum effective time determined in Section C1A. All experiments were repeated at least three times for statistical comparisons. The effect of morphine on CaMKII was compared with its inhibition of cAMP accumulation in SH-SY5Y cells.

C1C. The Dose-response of Morphine on the Inhibition of cAMP Accumulation

These experiments correlate the effect of morphine on CaMKII with its activation of opioid receptors, which together with the time course, demonstrate the mode of action of morphine on CaMKII activity. Individual groups of SH-SY5Y cells were treated with varying concentrations of morphine (0.1 nM to 100 µM) to determine the maximum effect and the $EC_{50}$ of morphine in inhibiting cAMP accumulation in these cells under the similar environment where activation of CaMKII was tested. All experiments were repeated at least three times for statistical comparisons.

C2.

Tests were performed to confirm whether CaMKII regulation is effected by an opioid agonist in vivo, and to correlate CaMKII expression and activity temporally to opioid tolerance. Subcutaneous implantation of morphine pellets (two 75 mg pellets) has been well established to produce antinociceptive tolerance in rats (e.g., Koob et al., 1992; Fitzgerald et al., 1996). This model eliminates possible opioid abstinence that can occur with intermittent administration methods, and minimizes animal stress associated with other methods of handling and injecting, which could lead to associative learning and memory (Granados-Soto et al., 2000).

Experimental Design: Individual groups of eight rats were prepared with i.th. catheters and allowed to recover for 5 to 7 days to ensure no motor deficiency due to catheter implantation. Rats then were implanted with morphine or placebo pellets subcutaneously. Morphine antinociceptive tests were performed before pelleting (day 0), and days 1, 3, 5, and 7 after pelleting. Dose-response curves of morphine (i.th. bolus injections) were constructed in rats receiving placebo or morphine pelleted. A significant decrease in % MPE at given doses from the pre-pelleting baseline values signifies the development of morphine antinociceptive tolerance. CaMKII expression and activity in lumbar segments of spinal cord was determined on days 0, 1, 3, 5, and 7 relative to morphine pelleting in order to establish the time course, which was compared to the onset of opioid antinociceptive tolerance.

Data interpretation: These studies temporally correlated CaMKII expression and/or activity with opioid tolerance.

An increased CaMKII activity at different time points was expected. However, it was not known whether CaMKII activity precedes or follows the onset of morphine tolerance. If CaMKII is an important factor in promoting opioid tolerance, then elevated CaMKII activity should precede the development of antinociceptive tolerance. Conversely, if CaMKII only is upregulated after the development of dependence, then its primary role is to maintain opioid tolerance. A persistent change before and after the development of morphine tolerance suggests that CaMKII is important in promoting and maintaining antinociceptive tolerance.

C3.

Tests were performed to correlate inhibition of CaMKII activity to the development of morphine antinociceptive tolerance. These studies established the role of CaMKII as a mediator of morphine antinociceptive tolerance. A selective CaMKII inhibitor (i.e., KN93) was employed to inhibit the spinal CaMKII, and CaMKII inhibition leading to reversal of morphine tolerance was tested. KN93 has been used to inhibit CaMKII activity in vivo (Corsi et al., 1998; Lu et al., 2000). As a control, KN92, an inactive structural analogue of KN93, also was tested.

C3A. Experimental Design for Inhibition of CaMKII by KN93

Separate groups of eight rats were implanted with i.th. catheters and allowed to recover for 5 to 7 days. Baseline nociceptive threshold was established prior to treatment. KN93 was administered by i.th. injection. At various treatment intervals (5, 15, 30, 60, 120 minutes), rats were sacrificed and the spinal cord taken for Western blotting analyses of CaMKII activity (i.e., its expression and β-actin content). Based on published data, a starting dose of 15 nmol (water soluble form, Calbiochem; dissolved in 5 ul saline) was administered (Corsi et al., 1998; Lu et al., 2000). Lower and higher doses of KN93 were used to determine the optimal dose for the inhibition of CaMKII. When the optimum dose was established, an expanded time course (up to 3 to 5 hours) was tested using the optimal dose, together with the negative control KN92 at the same dose. The dose and time course information were used to test the behavioral consequence of CaMKII inhibition by KN93.

C3B. Tests to Demonstrate that KN93 Reverses an Established Morphine Antinociceptive Tolerance in Rats, and that the Reversal Correlates with Inhibition of CaMKII Activity Individual groups of eight rats were implanted with i.th. catheters and allowed to recover for 5 to 7 days. The rats then were implanted with morphine or placebo pellets subcutaneously. At peak tolerance, determined as set forth above, KN93, KN92, or saline, was injected i.th. to the morphine-tolerant animals 15 minutes (i.e., 45 minutes before analgesic testing) before an i.th. challenge with acute morphine, to determine whether KN93 can acutely reverse morphine tolerance. KN93 dose-response effect was determined and compared to its effect in inhibiting CaMKII activity.

Data interpretation: A full dose response curve of KN93 was constructed and compared for its effects on morphine tolerance and spinal CaMKII inhibition. KN93 is the most selective, cell-permeable CaMKII inhibitor presently available. KN93 does not inhibit PKC or protein kinase A at doses administered. To ensure selectivity of KN93, however, the following tests were performed: 1) use the lowest possible doses that produce inhibition of spinal CaMKII and blockade of tolerance; and 2) administer the maximum dose of KN92 in experiments where KN93 is used. No available data supports a conclusion that KN93 inhibits PKC. However, because inhibition of PKC potentially modulates morphine antinociceptive tolerance, it was important to confirm that the effect of KN93 was not attributed to inhibition of PKC.

C4. Cell Culture and Morphine Treatment

Human neuroblastoma SH-SY5Y cells were maintained as a monolayer culture in Dulbecco's modified eagle medium (DMEM) supplemented with 10% fetal calf serum, 100 μg/ml streptomycin and 100 units/ml penicillin in 5% carbon dioxide, incubator maintained at 37° C. (Wang et al., 2000). Cells were plated into flasks a week before experiments Treatments were terminated at the designated times by replacing the medium with ice-cold phosphate buffered saline (PBS) on ice and subsequently rinsed with PBS three times. Cells then were used for cAMP assay or harvested as described in Section C10

C5. Assay of cAMP Accumulation

SH-SY5Y cells were plated into 24 well dish (17 mm in diameter) a week before the testing. For cAMP assays, monolayer cells were washed with PBS and incubated in serum-free DMEM medium at 37° C. for 15 minutes in the presence of 10 μM forskolin and 250 μM 3-isobutyl-1-methylxanthine (IBMX) with or without morphine. The reaction was quenched by adding hydrochloric acid (HCl) to a final concentration of 0.1 N, and intracellular cAMP was extracted and assayed using a radioimmunoassay (Amersham, Piscataway, N.J.) as described previously (Wang et al., 1994).

C6. Animals

Male Sprague-Dawley rats (250-350 g) were used in all experiments.

C7. Intrathecal Catheter Placement

For i.th. drug administration, rats were prepared according to the method described by Sakura et al. (1996). While under isoflurane anesthesia, an 8 cm length of PE10 tubing (32 gauge) was inserted through an incision made in the atlantooccipital membrane to the level of the lumbar enlargement. The catheter then was secured to the musculature at the site of incision, which then was closed. The rats were allowed 5 to 7 days to recover before experiments begin. Rats exhibiting signs of motor deficiency were euthanized. Intrathecally administered substances were dissolved in saline and administered in a volume of 5 μl through a tubing with calibrated length connecting the i.th. catheter with the injection syringe. Progress of the injection was monitored carefully by observing the movement of a small air bubble (1 μl in volume) through the tubing. The catheter was cleared by flushing with 9 μl saline. In all cases, a dye was injected into the cannula at the termination of the experiment to ensure correct i.th. placement.

C8. Morphine Pellet Implantation

To induce opioid tolerance, rats were subcutaneously implanted with two morphine pellets or placebo pellets (75 mg morphine base in each pellet; placebo contains no morphine; National Institute on Drug Abuse, Rockville, Md.) according to well-established protocols (e.g., Koob et al., 1992; Fitzgerald et al., 1996). Briefly, while under isoflurane anesthesia, a 1.5 cm incision was made on the back of the animal. Morphine and placebo pellets were implanted into the subcutaneous space and the incision was closed with wound clips. These pellets were left for less than 7 days unless otherwise indicated.

C9. Tissue Dissection for Western Blotting and Enzymatic Assays

Rats were sacrificed by carbon dioxide inhalation and decapitated. The spinal column was cut through at the S1/S2 level. A 16-gauge needle was inserted in the sacral vertebral canal, attached to a syringe containing ice-cold saline, and the spinal cord was ejected through the cervical opening. The spinal cord was placed on ice in a glass Petri dish and rapidly dissected using a dissecting microscope. For consistency, the lumbar enlargement corresponding to the L1 to L6 spinal segments was excised and used for all assays. Tissue samples were frozen immediately in liquid nitrogen and stored at −80° C. For PKC enzymatic assays, fresh tissues were used.

C10. Analyses of CaMKII Expression and Activity by Western Blot Analysis

Spinal segments or harvested SH-SY5Y cells were homogenized on ice in RIPA buffer (1% NP-40, 0.5% sodium deoxycholate, 0.1% sodium dodecyl sulfate (SDS), 5 mM EDTA in PBS, pH 7.4) (3 ml/g wet tissue, or 0.6 ml/10 cm dish) in the presence of protease inhibitors (0.05 mg/ml pepstatin, 0.05 mg/ml aprotinin, 0.1 mg/ml phenylmethylsulfonyl fluoride). This preparation then was incubated on a rotator at 4° C. for hours, and centrifuged at 48,000×g to remove the insoluble pellet. The supernatant was diluted in PBS for the measurement of protein content using a modified Bradford method and subject to separation by SDS-polyacrylamide gel electrophoresis (PAGE). For SDS-PAGE, supernatant samples were heated at 70° C. for 10 minutes in the loading buffer (2% SDS, 10% glycerol, 1% 2-mercaptoethanol, 0.01% bromophenol blue, 12.5 mM Tris-HCl, pH6.8), and 10-30 μg samples were loaded to each lane. Protein sizes were identified by protein weight markers (GIBCIO) loaded with samples on every gel. SDS-PAGE was performed under 100-140 V for 1-2 hours, and at the end of electrophoresis, the gel was disassembled and electroblotted onto PVDF membrane in Tris(25 mM)/SDS (0.1%)/glycin(192 mM)/methanol(20%) buffer. The membrane was washed and blocked in 5% nonfat milk in Tris (20 mM)-buffer saline (pH 7.6) with 0.1% Tween 20 (TTBS) for 2 hours, before incubated with a polyclonal antibody recognizing CaMKII α isoform from human, mouse, and rat tissues (1:500, Santa Cruz Biotechnology, Santa Cruz, Calif.), or a polyclonal antibody that recognizes active (pT286) CaMKII (pCaMKII) (1:3,000, Promega, Madison, Wis.). After three washes with TTBS, the membrane was incubated with horseradish peroxidase-linked donkey anti-rabbit IgG (1:1,000-5,000), and the blot was washed 3 more times with TTBS, and developed using ECL method (Amersham, Piscataway, N.J.). To control the amount of proteins in each sample, all membranes were probed with a monoclonal antibody against β-actin (Sigma, 1:20,000). ECL-detected bands were analyzed using a densitometer and Quantity One analysis program (BioRad, Hercules, Calif.).

C11. Evaluation of Morphine Analgesia and Antinociceptive Tolerance

Latency to warm water tail withdrawal response was determined in the manner described previously (Wang et al., 2001, Vanderah et al., 2001). The one-third of distal tail was immersed into a water bath maintained at 52° C. The latency to a rapid tail flick was recorded before and after i.th. morphine injection. A maximal cutoff of 10 seconds was applied to prevent tissue damage and was appropriate as the mean control latency is about 3-4 seconds. The data were converted to % MPE (maximal possible effect), defined as 100×(test-control)/(cutoff-control), where control was the predrug observation, test was the postdrug observation, and cutoff was 10 seconds. Dose-response curves were generated over time to determine the time of peak effect, the dose producing 50% MPE ($A_{50}$), and its confidence intervals (Tallarida et al., 1986). A significant decrease in response values (% MPE) from the pre-morphine baseline values signified the development of opioid antinociceptive tolerance.

Figure 5:
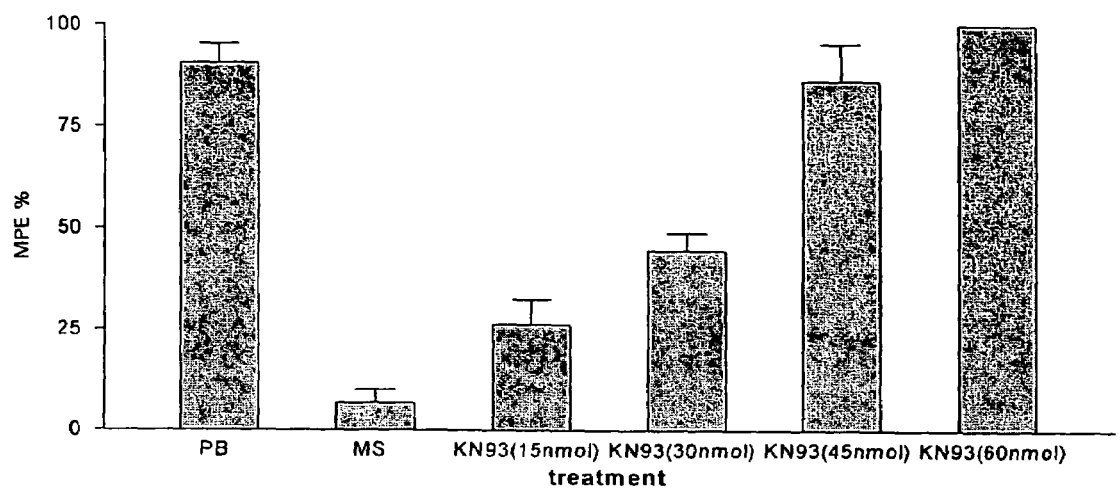
FIGS. 5-7 contain bar graphs showing that a CaMKII inhibitor dose-dependently reverses established opioid tolerance, prevents opioid tolerance, and prevents opioid dependence.

Additional in vivo tests corroborated initial test results showing that administration of a CaMKII inhibitor reduces or eliminates opioid tolerance and dependence. For example, in a mouse model of opioid tolerance due to chronic treatment with morphine (s.c. implantation of 75 mg controlled-release pellet, for up to seven days), morphine (given i.v., i.th., or perperally) produced significantly reduced antinociceptive effects (FIG. 5). FIG. 5 shows that KN93 dose-dependently reverses established opioid tolerance in a chronic model of opioid tolerance. Administration of a CaMKII inhibitor, i.e., KN93, effectively reversed the established tolerance to opioids (FIG. 5). The effect of KN93 is dose dependent. The same chronic treatment with morphine also produced drug dependence in mice, which was also reversed by acute administration of CaMKII inhibitors.

Figure 6:
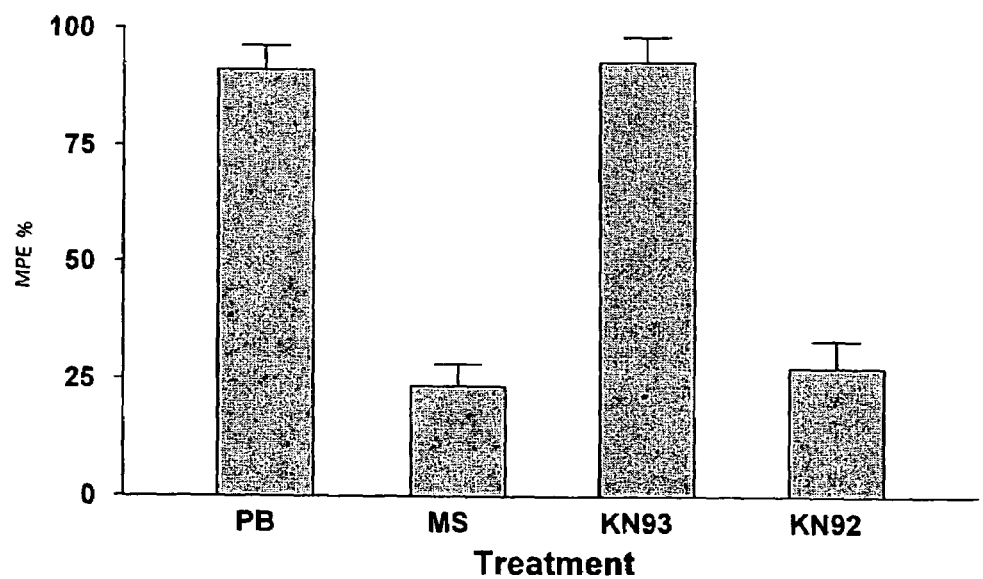
Figure 7:
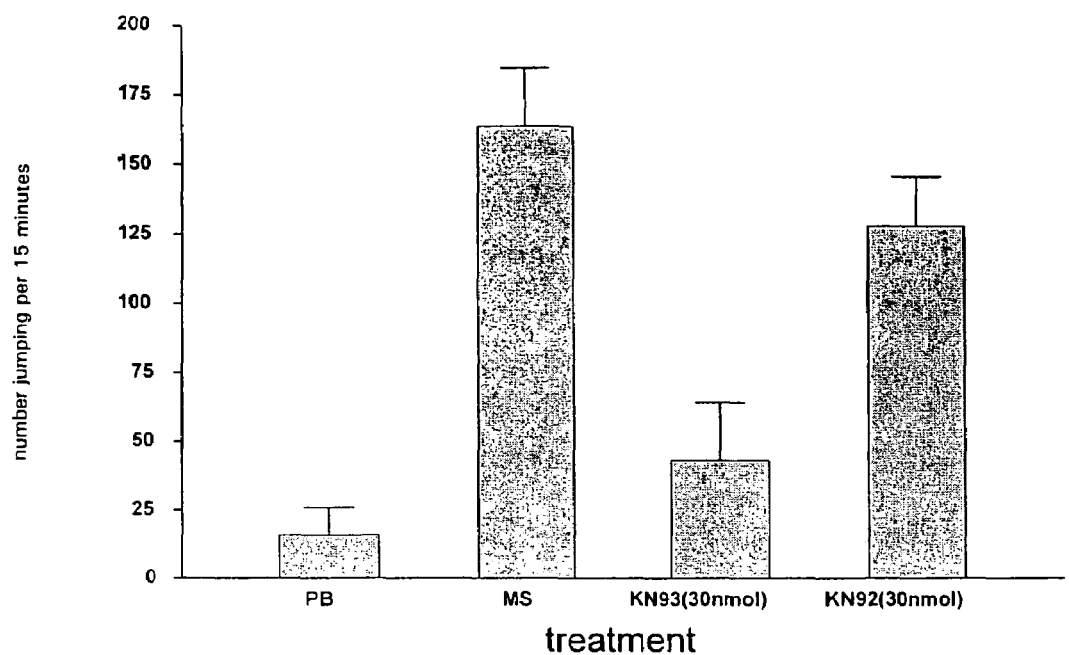
Figure 8:
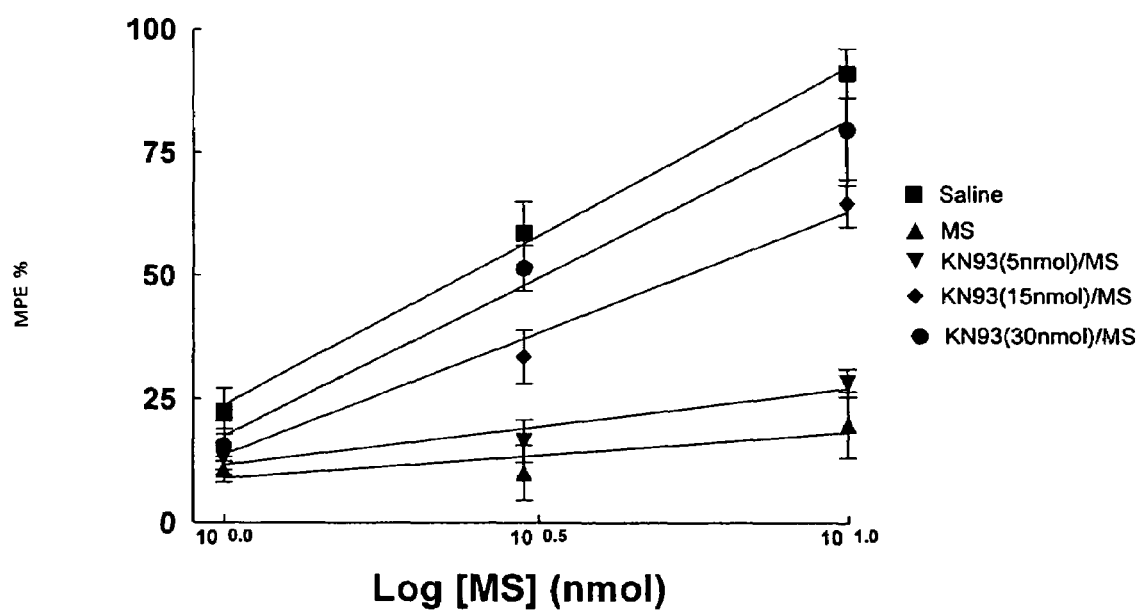
FIGS. 8-9 contain bar graphs showing that a CaMKII inhibitor reverses established opioid tolerance and reverses established opioid dependence.
Figure 9:
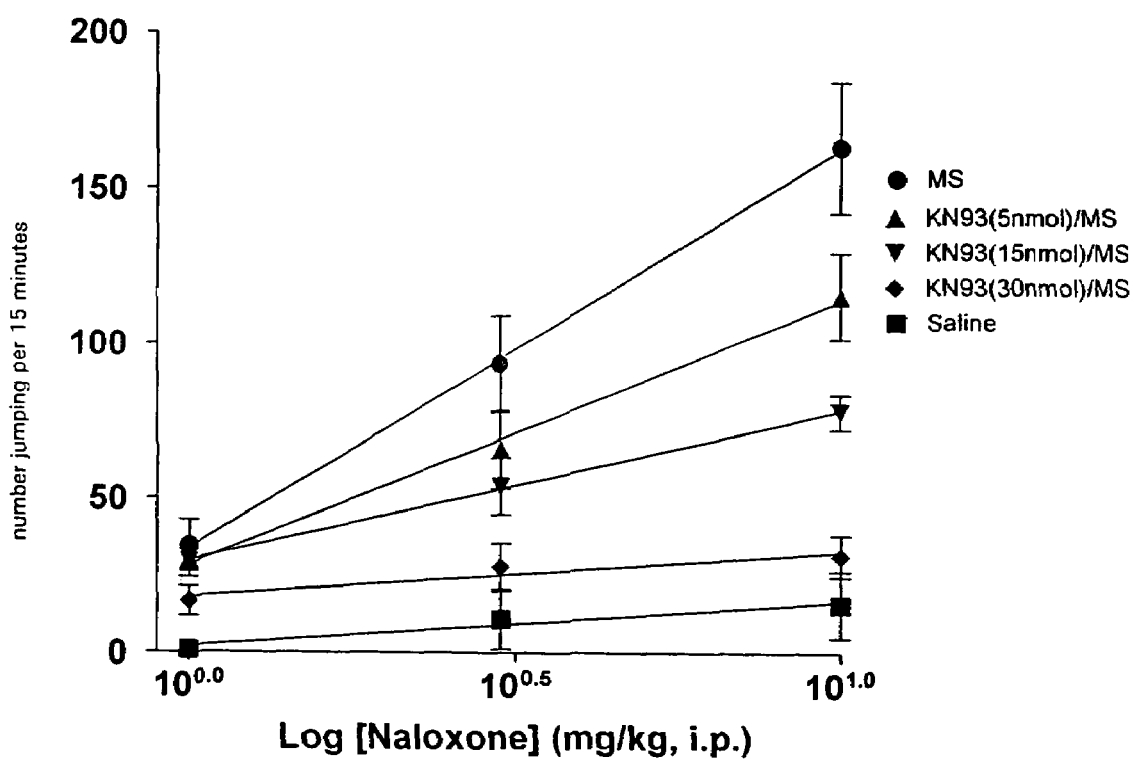

Acute tolerance and dependence model is a method commonly used by researchers. In this model, opioid tolerance and dependence are induced by a single s.c. injection of morphine (100 mg/kg). KN93 prevented the development of opioid tolerance and dependence when administered simultaneously with morphine (FIGS. 6 and 7). FIG. 6 shows that KN93 prevents opioid tolerance in an acute model of opioid tolerance. A close analogue, but inactive form KN92, does not affect opioid tolerance. FIG. 7 shows that KN93 dose-dependently prevents opioid dependence in an acute model of opioid dependence. In addition, the CaMKII inhibitor KN93 also was effective in reversing an already-established tolerance or dependence in the model (FIGS. 8 and 9). FIG. 8 shows that KN93 dose-dependently reverses established opioid tolerance in an acute model of opioid tolerance. FIG. 9 shows that KN93 dose-dependently reverses established opioid dependence in an acute model of opioid dependence. All effects are dose-dependent on the magnitude of inhibition of CaMKII.

The test results clearly demonstrate that a CaMKII inhibitor, e.g., KN93, does not affect morphine-induced analgesia. This is an important clinical finding because administration of a CaMKII inhibitor combined with administration of morphine does not interfere with the acute therapy of opiate analgesics and does not affect pharmacological actions of morphine.

On the basis of these test results, a CaMKII inhibitor reduces the dose of morphine and still produces same degree of analgesic action of morphine in opioid-tolerant state compared to a higher dose of morphine used alone. Lowering the dose of morphine can significantly reduce the addiction potential of morphine in patients.

These findings demonstrate that, when administered with a CaMKII inhibitor, morphine and other opiate analgesics produce significant analgesia using a lower dose of analgesic, and, therefore, the addiction potential of the opiate analgesic is reduced. These observations also indicate that the duration of the analgesic response of morphine can be significantly increased by administration of a CaMKII inhibitor.

The tests and data set forth herein show that a combination of an opiate analgesic and a CaMKII inhibitor can be administered to mammals in methods of treating pain. The opiate analgesic and a CaMKII inhibitor can be formulated in suitable excipients to provide a composition for oral administration or parenteral administration, for example. Such excipients are well known in the art. The active agents typically each are present in such a composition in an amount of about 0.1% to about 75% by weight, either alone or in combination.

Pharmaceutical compositions containing the active agents, i.e., an opiate analgesic and a CaMKII inhibitor, are suitable for administration to humans or other mammals. Typically, the pharmaceutical compositions are sterile, and contain no toxic, carcinogenic, or mutagenic compounds that would cause an adverse reaction when administered.

The present method can be accomplished using the active agents as described above, or as a physiologically acceptable salt, prodrug, or solvate thereof. The active agents, salts, prodrugs, or solvates can be administered as the neat compounds, or as a pharmaceutical composition containing either or both entities.

The active agents can be administered by any suitable route, for example by oral, buccal, inhalation, sublingual, rectal, vaginal, intracisternal through lumbar puncture, transuret oral, nasal, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™. Administration of the active agents can be performed before, during, or after the onset of pain.

The pharmaceutical compositions include those wherein the active ingredients are administered in an effective amount to achieve their intended purpose. More specifically, a "therapeutically effective amount" means an amount effective to prevent development of, to eliminate, or to alleviate pain. Determination of a therapeutically effective amount is well within the capability of those skilled in the art, especially in light of the detailed disclosure provided herein.

A "therapeutically effective dose" refers to the amount of the active agents that results in achieving the desired effect. Toxicity and therapeutic efficacy of such active agents can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained from such data can be used in formulating a range of dosage for use in humans. The dosage of the active agents preferably lies within a range of circulating concentrations that include the $ED_{50}$ with little or no toxicity. The dosage can vary within this range depending upon the dosage form employed, and the route of administration utilized.

The exact formulation, route of administration, and dosage is determined by an individual physician in view of the patient's condition. Dosage amounts and intervals can be adjusted individually to provide levels of active agents that are sufficient to maintain therapeutic or prophylactic effects.

The amount of active agents administered is dependent on the subject being treated, on the subject's weight, the severity of the affliction, the manner of administration, and the judgment of the prescribing physician.

Specifically, for administration to a human in the curative or prophylactic treatment of pain, oral dosages of an opiate analgesic and a CaMKII inhibitor, individually, generally are about 10 to about 200 mg daily for an average adult patient (70 kg), typically divided into two to three doses per day. Thus, for a typical adult patient, individual tablets or capsules contain about 0.1 to about 200 mg opioid analgesic and about 0.1 to about 50 mg CaMKII inhibitor, in a suitable pharmaceutically acceptable vehicle or carrier, for administration in single or multiple doses, once or several times per day. Dosages for intravenous, buccal, or sublingual administration typically are about 0.1 to about 10 mg/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The active agents of the present invention can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active agents into preparations that can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the active agents are administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an active agent of the present invention, and preferably from about 25% to about 90% of an active agent of the present invention. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of active agents, and preferably about 1% to about 50% of an active agents.

When a therapeutically effective amount of the active agents is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

Suitable active agents can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the active agents with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The active agents can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents, such as suspending, stabilizing, and/or dispersing agents.

Pharmaceutical compositions for parenteral administration include aqueous solutions of the active agent in water-soluble form. Additionally, suspensions of the active agents can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The active agents also can be formulated in rectal compositions, such as suppositories or retention enemas, e.g., containing conventional suppository bases. In addition to the formulations described previously, the active agents also can be formulated as a depot preparation. Such long-acting formulations can-be administered by implantation (for example, subcutaneously or intramuscularly) or by intramuscular injection. Thus, for example, the active agents can be formulated with suitable polymeric or hydrophobic materials (for example, as an emulsion in an acceptable oil) or ion exchange resins, or as sparingly soluble derivatives, for example, as a sparingly soluble salt.

In particular, the active agents can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. An active agent also can be injected parenterally, for example, intravenously, intramuscularly, subcutaneously, intrathecally, intracisternally, or intracoronarily. For parenteral administration, the active agent is best used in the form of a sterile aqueous solution which can contain other substances, for example, salts, or monosaccharides, such as mannitol or glucose, to make the solution isotonic with blood.

For veterinary use, the active agents are administered as a suitably acceptable formulation in accordance with normal veterinary practice. The veterinarian can readily determine the dosing regimen and route of administration that is most appropriate for a particular animal.

As stated above, morphine is one of the most potent analgesics, and is widely used for pain management in several disease conditions, including cancer. A major problem in the use of morphine, and other opiate analgesics, is their potential to produce sedation tolerance/dependent, and respiratory depressions, and to cause addiction.

It has been discovered that using a CaMKII inhibitor alone or in combination with an opiate analgesic prevents, or reverses, tolerance to opioid analgesics, thus potentiating the analgesic action of the analgesic. The combined opiate analgesic-CaMKII inhibitor treatment can be used, for example, in cancer pain, neuropathic pain, and other chronic pain syndromes.

By using less morphine, the addiction potential of an opiate analgesic in patients can be reduced significantly. The administration of a CaMKII inhibitor to an individual undergoing opiate analgesic treatment, therefore, reduces or eliminates tolerance to opiate analgesics.

REFERENCES

M. D. Aceto et al., *Eur J Pharmacol*, 123(3):387-93 (1986).
J. R. Arden et al., *J Neurochem* 65:1636-1645 (1995).
P. Avenet et al., *Neurosci Lett*, 223(2):133-6 (1997).
E. J. Bilsky et al., *J Pharmacol Exp Ther* 277:484-490 (1996).
J. A. Blendy et al., *J Mol Med* 76:104-110 (1998).
I. Bruggemann et al. *Brain Res Mol Brain Res* 85:239-250 (2000).
T. J. Coderre et al., *Eur J Neurosci* 6:1328-1334 (1994).
L. Corsi et al., *J Neurochem* 70:1898-1906 (1998).A. Cowan et al., *J Pharmacol Exp Ther*, 246(3):950-5 (1988).
A. Cowan et al., *J Pharmacol Exp Ther*, 246(3):950-5 (1988).
G. E. DeLander et al., *J Pharmacol Exp Ther*, 231(1):91-6 (1984).
G. H. Fan et al., *Mol Pharmacol* 56:39-45 (1999).
A. Fields et al., *Life Sci* 61:595-602 (1997).
K. M. Foley, Handbook of Experimental Pharmacology, Springer-Verlag, Berlin (1993).
Y. Fukagawa et al., *Eur J Pharmacol*, 170(1-2):47-51 (1989).
K. Fukunaga et al., *J Biol Chem* 267:22527-22533 (1992).
S. A. Glantz, Primer of Biostatistics, McGraw-Hill, New York, p. 473 (1981).
V. Granados-Soto et al., *Pain* 85:395-404 (2000).
Himmelsbach, *Fed Proc*, 2:201-203 (1943).
Q. Jiang et al., *Prog Clin Biol Res*, 328:449-52 (1990).
J. L. Katz et al., Behavioral Analysis of Drug Dependence, ed. S. R. Goldberg et al., Vol. Ch. 8, pp. 287-327, Academic Press, Orlando (1986).
Y. Kitamura et al., *J Neurochem* 61:100-109 (1993).
T. Koch et al., *J Neurochem* 69:1767-1770 (1997).
L. Lou et al., *Mol Pharmacol* 55:557-563 (1999).
L. Lu et al., *Neurosci Lett* 291:191-195 (2000).
R. Maldonado et al., *J Pharmacol Exp Ther*, 261(2):669-77 (1992).
R. Maldonado et al., Neurobiological Mechanisms of Opiate Withdrawal, ed. R. Maldonado et al., Vol. Ch. 5, pp. 77-124, Springer, New York. (1996).
R. Maldonado et al., *Science* 273:657-659 (1996)
J. Mao et al., *Pain* 61:353-364 (1995).
H. W. Matthes et al., *Nature*, 383(6603): 819-23 (1996).
M. Mayford et al., *Science* 274:1678-1683 (1996).
A. Mestek et al., *J Neurosci* 15:2396-2406 (1995).
M. Narita et al., *Psychopharmacology*, 111(4):423-6 (1993).
M. Narita et al., *Eur J Pharmacol* 280:R1-3 (1995).
M. Narita et al., *Pharmacol Ther*, 89(1):1-15 (2001).
M. Narita et al., *J Biol Chem* 276:15409-15414 (2001).
R. Nehmad et al., *Mol Pharmacol* 22:389-394 (1982).
E. J. Nestler, *Neuropsychopharmacology* 11:77-87 (1994).
E. J. Nestler, *Curr Opin Neurobiol* 7:713-719 (1997).
E. J. Nestler et al., *Science* 278:58-63 (1997).
S. Niu et al., *Jpn J Pharmacol* 84:412-417 (2000).
Z. Z. Pan, *Trends Pharmacol Sci*, 19(3):94-8 (1998).
P. S. Portoghese et al., *J Med Chem*, 23(3):233-4 (1980).

J. M. Quillan et al., *J Pharmacol Exp Ther* 302:1002-1012 (2000).

C. P. Quock et al., *Br J Addict Alcohol Other Drugs,* 63:261-270 (1968).

S. Sakura et al., *Anesthesiology* 85:1184-1189 (1996).

S. K. Sharma et al., *Proc Natl Acad Sci USA* 72:3092-3096 (1975).

J. Shen et al., *Synapse* 38:322-327 (2000).

D. G. Standaert et al., *J Comp Neurol,* 343(1):1-16 (1994).

S. Strack et al., *J Biol Chem* 273:20689-20692 (1998).

S. Strack et al., *J Biol Chem* 275:23798-23806 (2000).

T. Suzuki et al., *Life Sci,* 50(12):849-56 (1992).

T. Suzuki et al., *Pharmacol Biochem Behav,* 57(1-2):293-9 (1997).

A. E. Takemori et al., *Eur J Pharmacol,* 70(4):445-51 (1981).

R. J. Tallarida et al., *Pharmacology, Biochemistry & Behavior* 38:673-675 (1986).

T. M. Tzschentke et al., *Neurosci Lett,* 193(1):37-40 (1995).

T. W. Vanderah et al., *J Neurosci* 21:279-286 (2001).

J. M. Van Ree et al., *Pharmacol Rev,* 51:342-396 (1999).

M. A. Varney et al., *J Pharmacol Exp Ther,* 279(1):367-78 (1996).

Z. Wang et al., *Eur J Pharmacol* 371:1-9 (1993).

Z. Wang et al., *Life Sci* 54:L339-350 (1994).

Z. Wang et al., *Eur J. Pharmacol.* 389:165-171 (2000).

Z. Wang et al., *J Neurosci* 21:1779-1786 (2001).

S. J. Ward et al., *J Pharmacol Exp Ther,* 220:494-498 (1982).

M. Watanabe et al., *J Comp Neurol,* 338:377-390 (1993).

J. T. Williams et al., *Physiol Rev,* 81(1):299-343 (2001).

S. Yokota et al., *J Neurochem* 77:618-627 (2001).

K. P. Zeitz et al., *Pain* 94:245-253 (2001).

Modifications and variations of the invention as hereinbefore set forth can be made without departing from the spirit and scope thereof, and, therefore, only such limitations should be imposed as are indicated by the appended claims.

What is claimed is:

1. A method for reducing tolerance to an opiate analgesic in an individual undergoing opiate analgesic therapy comprising administering intrathecally to an individual an effective amount of KN93 (2-[N-(2-hydroxyethyl)]-N-(4-methoxybenzenesulfonyl)]amino-N-(4-chlorocinnamyl)-N-methylbenzylamine) which inhibits the activity of spinal calmodulin dependent protein kinase II.

* * * * *